US012125216B2

(12) United States Patent
Fang et al.

(10) Patent No.: US 12,125,216 B2
(45) Date of Patent: Oct. 22, 2024

(54) MOTION BASED PATHOGEN DETECTION USING A FLUIDIC IMAGER

(71) Applicant: McMaster University, Hamilton (CA)

(72) Inventors: Qiyin Fang, Grimsby (CA); Jessica Kun, Mississauga (CA); Marek Smieja, Hamilton (CA)

(73) Assignee: McMaster University, Hamilton (CA)

( * ) Notice: Subject to any disclaimer, the term of this patent is extended or adjusted under 35 U.S.C. 154(b) by 489 days.

(21) Appl. No.: 17/304,337

(22) Filed: Jun. 18, 2021

(65) Prior Publication Data

US 2021/0398296 A1 Dec. 23, 2021

Related U.S. Application Data

(60) Provisional application No. 63/040,652, filed on Jun. 18, 2020.

(51) Int. Cl.
| | |
|---|---|
| *G06T 7/246* | (2017.01) |
| *B01L 3/00* | (2006.01) |
| *G01N 33/487* | (2006.01) |
| *G01N 33/49* | (2006.01) |

(Continued)

(52) U.S. Cl.
CPC ........ *G06T 7/248* (2017.01); *B01L 3/502715* (2013.01); *G01N 33/48735* (2013.01); *G01N 33/492* (2013.01); *G06T 7/0012* (2013.01); *G06T 7/215* (2017.01); *G01N 2333/195* (2013.01); *G06T 2207/30024* (2013.01)

(58) Field of Classification Search
CPC ....... G06T 7/248; G06T 7/215; G06T 7/0012; G06T 2207/30024; B01L 3/502715; G01N 33/48735; G01N 33/492; G01N 2333/195
See application file for complete search history.

(56) References Cited

U.S. PATENT DOCUMENTS

| | | | | |
|---|---|---|---|---|
| 9,495,742 | B2 * | 11/2016 | Lagae | G01N 15/1484 |
| 9,743,020 | B2 * | 8/2017 | Zheng | H04N 25/48 |
| 10,201,277 | B2 * | 2/2019 | Ruppersberg | A61B 5/6858 |

(Continued)

OTHER PUBLICATIONS

Lin et al., "Urine analysis in microfluidic devices.," Analyst, vol. 136, No. 13, pp. 2669-2688, Jul. 2011.

(Continued)

*Primary Examiner* — Gregory M Desire
(74) *Attorney, Agent, or Firm* — Bereskin & Parr LLP

(57) ABSTRACT

Systems, methods and devices for detecting a presence of an analyte in a fluid sample are described herein. The devices include a microfluidic module having a microfluidic channel configured to receive the fluid sample at an inlet thereof and direct the fluid sample towards an outlet thereof. The devices also include an image sensor positioned removably abutting the microfluidic module. The image sensor is positioned laterally between the inlet and the outlet of the microfluidic channel and below a lower surface of the microfluidic channel. The image sensor is communicatively coupled to a processor that is configured to receive signal data from the image sensor. The devices also include a light source configured to direct light through the fluid sample and towards the image sensor as the fluid sample passes through the microfluidic channel. The image sensor receives the light and outputs the signal data to the processor.

20 Claims, 8 Drawing Sheets

(51) Int. Cl.
  *G06T 7/00*    (2017.01)
  *G06T 7/215*   (2017.01)

(56) References Cited

U.S. PATENT DOCUMENTS 10,229,340 B2 *  3/2019  Loui .................. G06T 7/215
10,518,261 B2 * 12/2019  Lee .................... B01L 3/5027
11,484,239 B2 * 11/2022  Haeusser ............ A61B 5/361
11,635,379 B2 *  4/2023  Palanisami ....... B01L 3/502715
                                                    422/82.07

OTHER PUBLICATIONS

Goyal et al., "Electrochemical sensor for the simultaneous determination of caffeine and aspirin in human urine samples," J. Electroanal. Chem., vol. 655, No. 2, pp. 97-102, Jun. 2011.

Kuswandi et al., "Optical sensing systems for microfluidic devices: A review," Anal. Chim. Acta, vol. 601, No. 2, pp. 141-155, Oct. 2007.

Simerville et al., "Urinalysis: a comprehensive review.," Am. Fam. Physician, vol. 71, No. 6, pp. 1153-1162, Mar. 2005.

Kissinger et al., "Trichomonas vaginalis: a review of epidemiologic, clinical and treatment issues," BMC Infect. Dis., vol. 15, No. 1, p. 307, Dec. 2015.

Garber et al., "The laboratory diagnosis of Trichomonas vaginalis.," Can. J. Infect. Dis. Med. Microbiol.=J. Can. des Mal. Infect. la Microbiol. medicale, vol. 16, No. 1, pp. 35-38, Jan. 2005.

Silver et al., "Trichomonas vaginalis as a Cause of Perinatal Morbidity," Sex. Transm. Dis., vol. 41, No. 6, pp. 369-376, Jun. 2014.

Mann et al., "Trichomoniasis in Pregnancy and Mental Retardation in Children," Ann. Epidemiol., vol. 19, No. 12, pp. 891-899, Dec. 2009.

Gaydos et al., "Rapid and point-of-care tests for the diagnosis of Trichomonas vaginalis in women and men.," Sex. Transm. Infect., vol. 93, No. S4, pp. S31-S35, Dec. 2017.

Davenport et al., "New and developing diagnostic technologies for urinary tract infections," Nat. Rev. Urol., vol. 14, No. 5, pp. 296-310, May 2017.

Mejuto et al., "Automated Flow Cytometry: An Alternative to Urine Culture in a Routine Clinical Microbiology Laboratory?," Int. J. Microbiol., vol. 2017, pp. 1-8, Sep. 2017.

Sorlozano et al., "Evolution of the resistance to antibiotics of bacteria involved in urinary tract infections: A 7-year surveillance study," Am. J. Infect. Control, vol. 42, No. 10, pp. 1033-1038, Oct. 2014.

Broeren et al., "Screening for urinary tract infection with the Sysmex UF-1000i urine flow cytometer.," J. Clin. Microbiol., vol. 49, No. 3, pp. 1025-1029, Mar. 2011.

McIsaac et al., "The impact of empirical management of acute cystitis on unnecessary antibiotic use.," Arch. Intern. Med., vol. 162, No. 5, pp. 600-605, Mar. 2002.

Yasuma et al., "Evaluation of a UF-1000i screening method to identify the bacteriuria for cultures and susceptibility testing," Rinsho Byori., vol. 60, No. 11, pp. 1070-1074, Nov. 2012.

Delanghe, "New Screening Diagnostic Techniques in Urinalysis," Acta Clin. Belg., vol. 62, No. 3, pp. 155-161, Jun. 2007.

Ozcan et al., "Lensless Imaging and Sensing," Annu. Rev. Biomed. Eng., vol. 18, No. 1, pp. 77-102, Jul. 2016.

Hill, "Parasites in motion: flagellum-driven cell motility in African trypanosomes," Curr. Opin. Microbiol., vol. 13, No. 4, pp. 459-465, Aug. 2010.

Huppert et al., "6: Comparison of diagnostic methods for Trichomonas vaginalis," J. Adolesc. Heal., vol. 40, No. 2, p. S8, Feb. 2007.

Dupire et al., "Full dynamics of a red blood cell in shear flow.," Proc. Natl. Acad. Sci. U. S. A., vol. 109, No. 51, pp. 20808-20813, Dec. 2012.

Zivkovic, "Improved Adaptive Gaussian Mixture Model for Background Subtraction," 2004.

Schindelin et al., "Fiji: an open-source platform for biological-image analysis," Nat. Methods, vol. 9, No. 7, pp. 676-682, Jul. 2012.

Schindelin et al., "The ImageJ ecosystem: An open platform for biomedical image analysis," Mol. Reprod. Dev., vol. 82, No. 7-8, pp. 518-529, Jul. 2015.

FFmpeg Developers, "FFmpeg Tool (V.4.2)." 2019.

Schuergers et al., "Cyanobacteria use micro-optics to sense light direction.," Elife, vol. 5, Feb. 2016.

Shanmugam et al., "Lensless fluorescence imaging with height calculation," J. Biomed. Opt., vol. 19, No. 1, p. 016002, Jan. 2014.

Ji et al., "3D Convolutional Neural Networks for Human Action Recognition," IEEE Trans. Pattern Anal. Mach. Intell., vol. 35, No. 1, pp. 221-231, Jan. 2013.

Fang et al., "An on-chip instrument for white blood cells classification based on a lens-less shadow imaging technique," PLoS One, vol. 12, No. 3, p. e0174580, Mar. 2017.

Storey et al., "Utilization of computer processed high definition video imaging for measuring motility of microscopic hematode stages on a quantitative scale: 'The Worminator,'" Int. J. Parasitol. Drugs Drug Resist., vol. 4, No. 3, pp. 233-243, Dec. 2014.

Mor et al., "Parasitic Diseases of Urinary Tract," Middle Black Sea J. Heal. Sci., vol. 2, No. 3, pp. 11-18, 2016.

* cited by examiner

MOTION BASED PATHOGEN DETECTION USING A FLUIDIC IMAGER

This application claims the benefit of U.S. Provisional Application Ser. No. 63/040,652, filed Jun. 18, 2020, which is hereby incorporated herein by reference.

TECHNICAL FIELD

This disclosure relates generally to biological analyte detection, and more specifically, to imaging-based pathogen detection in a fluid sample.

BACKGROUND

Fluidic sample analysis is a critical diagnostic tool used in health care. Currently there are separate tests available for the detection of for different pathogens, and they can be expensive and slow to process. In many cases, many negative samples are being processed, which is an excessive waste of time and resources. For example, trichomoniasis is a very prominent sexually transmitted infection (STI) that is often underdiagnosed due to the lack of an effective test. The gold standard for bacterial identification is culturing the samples as they come through the regional microbiological laboratory. This typically takes about 48 hours and about 70% of samples turn out to be negative. A pre-screen is necessary to eliminate these samples. For trichomoniasis, wet mount microscopy, the most common identification method, is unreliable and can take up to a week if the sample needs to be cultured before being tested.

Flow cytometry is being developed and tested as preliminary screens for urinalysis, and point-of-care tests have been developed for the diagnosis of trichomoniasis, bacterial vaginosis and vulvovaginal candidiasis. Though there has been progress in this area, rapid and cost-effective diagnosis is not yet routine. An image-based flow cytometry tool like the Iris iQ200 is an FDA approved automated urine microscopy analyzer that has been tested as an alternative to manual microscopy. In the Iris iQ200, urine samples are hydrodynamically focused between two layers of fluid in order to create a planar flow. Particles in the urine are analyzed as they pass under an objective lens that is used to focus on the particles and capture 500 frames per sample. The images are captured on a charge-coupled device (CCD) camera and a neural network algorithm classifies particles based on shape, size, texture and contrast. This instrument is being used in clinics as a urine analyzer but is not a low-cost point of care tool. This setup is a larger benchtop instrument.

Other microfluidics, lensless imaging approaches have also been developed. These technologies integrate expensive imager modules and the sample handling modules together. They also use still images to perform morphological based analysis.

Accordingly, there is a need for new systems, methods and devices of biological analyte detection.

SUMMARY

In accordance with a broad aspect, an optofluidic device for detecting a presence of an analyte in a fluid sample is described herein. The optofluidic device includes a microfluidic module having a microfluidic channel. The microfluidic channel has an upper surface, a lower surface and two opposed side surfaces each coupled to and extending between the upper surface and the lower surface. The microfluidic channel is configured to receive the fluid sample at an inlet thereof and direct the fluid sample towards an outlet thereof. The device also includes an image sensor removably abutting the microfluidic module. The image sensor is positioned laterally between the inlet and the outlet and below the lower surface of the microfluidic channel. The image sensor is communicatively coupled to a processor that is configured to receive signal data from the image sensor. The device also includes a light source configured to direct light through the fluid sample and towards the image sensor as the fluid sample passes through the microfluidic channel. The image sensor is configured to receive the light after it passes through the fluid sample and output the signal data to the processor to be used by the processor to detect the presence of the analyte in the fluid sample.

In at least one embodiment, the microfluidic module is positioned above the image sensor and a lower surface of the microfluidic module removably abuts a top surface of the image sensor.

In at least one embodiment, the lower surface of the microfluidic module is unadhered to the top surface of the image sensor providing for the microfluidic module to be replaceable.

In at least one embodiment, the microfluidic module is positioned between the light source and the image sensor.

In at least one embodiment, the light source is a non-coherent light source.

In at least one embodiment, the device also includes a clamping system configured to maintain the microfluidic module and the image sensor in pressurized contact with each other.

In at least one embodiment, the clamping system is configured to apply a downward force on the microfluidic module and an upward force on the image sensor to maintain the microfluidic module and the image sensor in the pressurized contact with each other.

In at least one embodiment, the clamping system is configured to maintain the microfluidic module and the image sensor in the pressurized contact with each other and to release the microfluidic module and the image sensor from each other after the fluid sample flows through the microfluidic channel.

In at least one embodiment, the microfluidic module includes a top layer and a bottom layer, the top layer being plasma bonded to the bottom layer and the bottom layer having a thickness that is less than or equal to 20 mm.

In at least one embodiment, the processor is configured to receive the signal data from the image sensor and based on the signal data, detect the presence of the analyte in the fluid sample.

In at least one embodiment, the processor is configured to detect the presence of the analyte in the fluid sample by: converting the signal data from the image sensor to image data; creating a video based on the image data; and analyzing features of the video to detect the presence of the analyte.

In at least one embodiment, the processor is configured to analyze features of the video by operating a tracking algorithm.

In at least one embodiment, the processor is further configured to analyze one or more frames of the video to detect moving objects in the video.

In at least one embodiment, the processor is further configured to, based on summing multiple frames of the video, detect the presence of the analyte based on motion-based biomarkers of the analyte.

In at least one embodiment, the analyte is *Trichomonas vaginalis* and the processor is configured to detect the presence of the *Trichomonas vaginalis* based on motion-based biomarkers specific to *Trichomonas vaginalis*.

In at least one embodiment, the analyte has a non-spherical shape, and the processor is configured to measure an elliptical ratio of shadow images of the analyte over multiple frames of the video to detect the presence of the analyte.

In at least one embodiment, the analyte is red blood cells or white blood cells.

In at least one embodiment, the analyte is a bacteria and the processor is configured to detect the presence of the bacteria based on motion-based biomarkers specific to the bacteria acquired over multiple frames of the video.

In at least one embodiment, the processor is configured to detect the presence of objects that are smaller than a resolution limit of the system using subpixel motion between frames.

In at least one embodiment, the fluid sample is a bodily fluid sample.

In at least one embodiment, the analyte is an organism that generates a unique movement pattern.

In at least one embodiment, the motion-based biomarker is used to determine whether the organism is alive.

In at least one embodiment, the analyte has a non-spherical shape as it flows through the field of the view of the image sensor.

In at least one embodiment, the analyte is smaller than a height of the microfluidic channel to provide for it to flow freely through the microfluidic channel and larger than one half of a width of a pixel on the image sensor.

In accordance with another broad aspect, a method of detecting a presence of an analyte in a fluid sample is described herein. The method includes forming a microfluidic module having a microfluidic channel, the microfluidic channel having an upper surface, a lower surface and two opposed side surfaces each coupled to and extending between the upper surface and the lower surface, the microfluidic channel being configured to receive the fluid sample at an inlet thereof and direct the fluid sample towards an outlet thereof. The method also includes positioning an image sensor between the inlet and the outlet and below the lower surface of the microfluidic channel, the image sensor being communicatively coupled to a processor configured to receive signal data from the image sensor. The method also includes directing a fluid containing the analyte through the microfluidic channel. The method also includes directing light from a light source through the fluid sample and towards the image sensor as the fluid sample passes through the microfluidic channel, the image sensor being configured to receive the light after it passes through the fluid sample and output the signal data to the processor to be used by the processor to detect the presence of the analyte in the fluid sample.

In at least one embodiment, devices that can inhibit negative samples from further processing are described that may provide more effective treatment and significantly reduce overall management costs including screening and treatment relative to prior art devices.

In at least one embodiment, a point-of-care device is described herein that may reduce turnaround time for samples, decrease health care costs, and decrease workload in labs. In at least one embodiment, the devices described herein can be implemented as a point-of-care device in, for example, hospital rooms and clinics to reduce the number of samples being sent to labs. In at least one embodiment, the devices described herein may provide for personalized diagnosis as the clinical situation of the patient is immediately apparent. In at least one embodiment, the devices described herein may be used by organizations and/or people that travel to remote and/or low resource regions for medical aid.

In at least one embodiment, the devices described herein provide a lensless imaging approach that provides for high throughput measurements. In at least one embodiment, the devices described herein a design that separates the imager and the sample handling fluidic module. In at least one embodiment, the devices described herein provide for motion and/or morphological features to be used as biomarkers for diagnosis. In at least one embodiment, the devices described herein provide for specific motion-based biomarkers and related algorithms for trichomonas vaginalis diagnosis. In at least one embodiment, the devices described herein provide for specific motion based biomarkers and related algorithms for red blood cells and white blood cells diagnosis. In at least one embodiment, the devices described herein provide for specific motion based biomarkers and related algorithms for bacteria diagnosis.

These and other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1A:
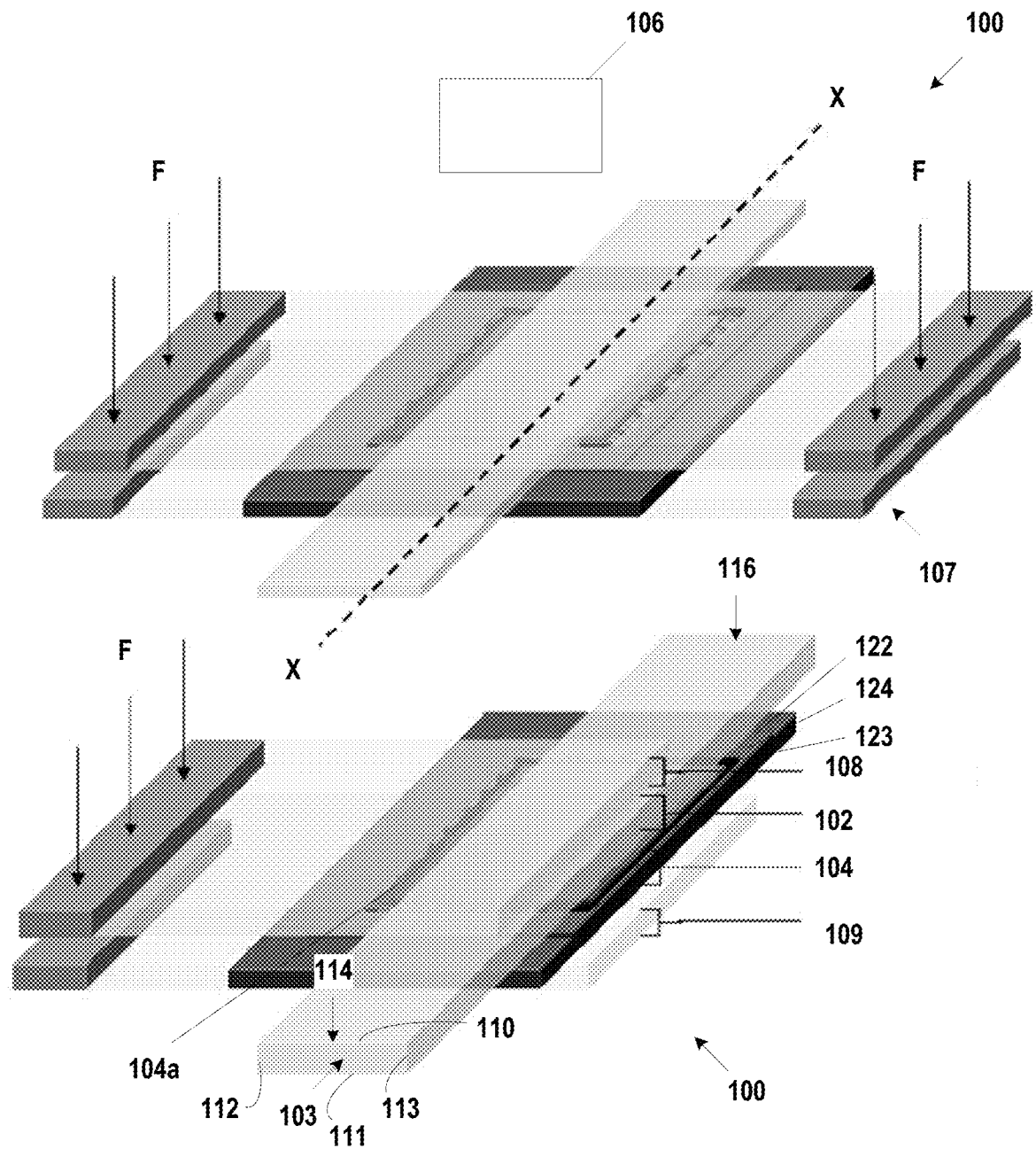
FIG. 1A is a perspective view of a schematic of an optofluidic imaging device, according to at least one embodiment described herein, and a perspective cross-section view thereof.

Further aspects and features of the example embodiments described herein will appear from the following description taken together with the accompanying drawings.

DETAILED DESCRIPTION

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter is not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term, such as 1%, 2%, 5%, or 10%, for example, if this deviation does not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive—or. That is, "X and/or Y" is intended to mean X, Y or X and Y, for example. As a further example, "X, Y, and/or Z" is intended to mean X or Y or Z or any combination thereof. Also, the expression of A, B and C means various combinations including A; B; C; A and B; A and C; B and C; or A, B and C.

At least one of the embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The following description is not intended to limit or define any claimed or as yet unclaimed subject matter. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

Fluidic human biological sample analysis such as blood, urine and vaginal swab testing is an essential clinical diagnostic tool. The presence of targeted analytes, or particulates, typically analyzed through microscopic urinalysis or cell culture, can be indicative of many diseases, including bacterial, parasitic, and yeast infections, as well as more serious conditions like bladder cancer. Current diagnostic methods are usually centralized and limited by high cost, inconvenience, and poor sensitivity. Herein, a lensless projection imaging optofluidic platform is described with motion-based analyte analysis to rapidly detect analytes or constituents of the fluid sample (e.g. urine) without the need for concentration or amplification through culture. The devices include a removable microfluidic module having a microfluidic channel that ensures that urine samples do not cross contaminate and the lens-free projection video is captured and processed by a low-cost integrated microcomputer.

A motion tracking and analysis algorithm is also described herein and used to identify and track moving analytes in the flowing fluid sample. Motion characteristics of the analytes have been used as biomarkers to detect different analytes (e.g. urine species) in near real-time. For example, the systems and devices described herein may provide for detection of red and white blood cells, *Trichomonas vaginalis,* crystals, casts, yeast, bacteria and the like. the systems and devices described herein have the potential to be implemented for timely, point-of-care detection of a wide range of disorders in hospitals, clinics, long-term care homes, and in resource-limited regions.

Figure 1B:
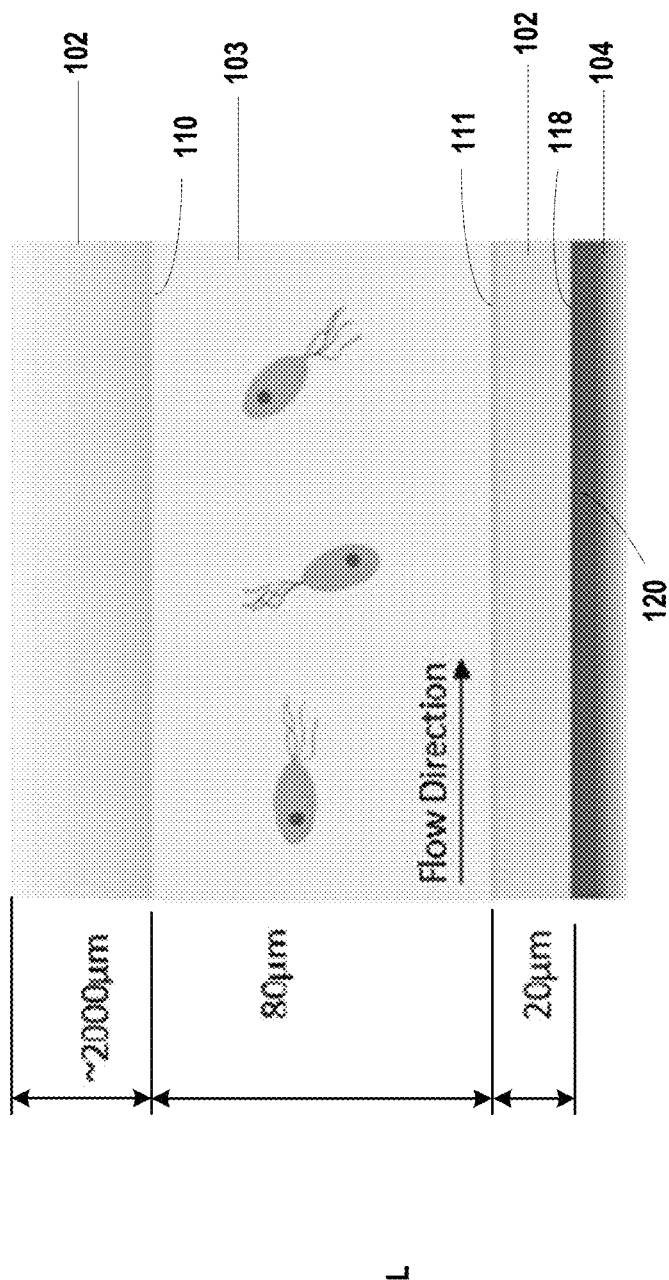
FIG. 1B is a side cross-section view of the optofluidic imaging device of FIG. 1A.
Figure 1C:
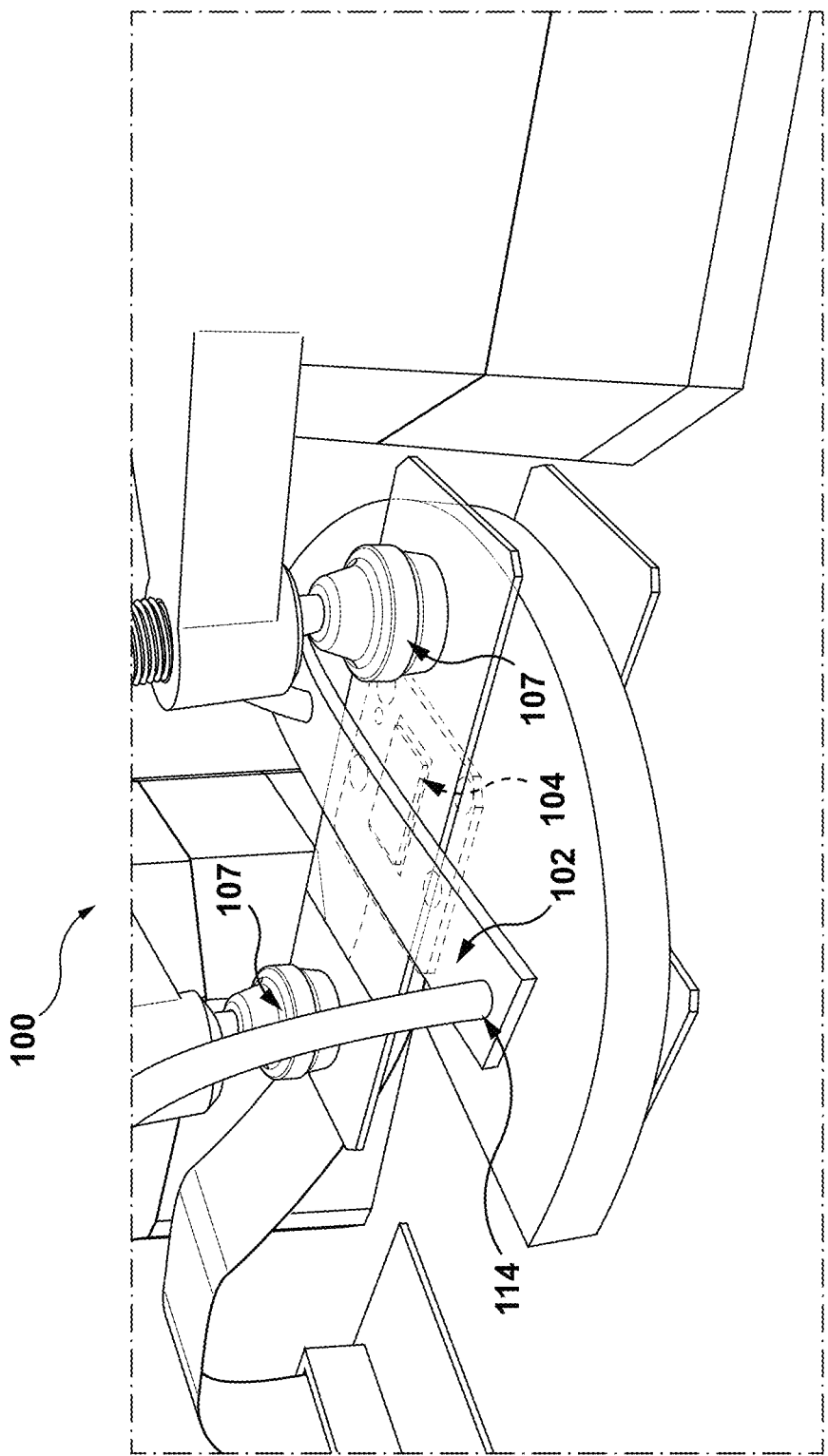
FIG. 1C is a photograph of the optofluidic imaging device of FIG. 1A.

FIG. 1A shows a perspective view of an optofluidic imaging device 100, according to at least one embodiment described herein. FIG. 1B is a cross-section view of the optofluidic imaging device 100 of FIG. 1A along line X-X. FIG. 1C is a photograph of the optofluidic imaging device of FIG. 1A.

Optofluidic device 100 comprises a microfluidic module 102 having a microfluidic channel 103 therein. Microfluidic channel 103 is configured to receive a fluid sample for imaging using the device 100. Optofluidic device 100 also comprises an image sensor 104. Image sensor 104 is positioned to abut the microfluidic module 102. Optofluidic device 100 also comprises a light source 106 positioned above the microfluidic module 102 and the image sensor 104. Microfluidic module 102 is typically positioned between light source 106 and image sensor 104 such that light emitted from light source 106 passes through microfluidic module 102, microfluidic channel 103 and any fluid sample therein and is received by image sensor 104 (e.g. by a top surface 104a of image sensor 104).

In at least one embodiment, optofluidic device 100 also includes a pressure mechanism 107 that is configured to apply a force to one or both of the microfluidic module 102 and image sensor 104. In the embodiment shown in FIG. 1A, pressure mechanism 107 includes a top glass slide 108 and a bottom glass slide 109. Top glass slide 108 and bottom glass slide 109 apply a force F to microfluidic module 102 and image sensor 104, respectively, to maintain microfluidic module 102 and image sensor 104 being in pressurized contact with each other. Herein, the term "pressurized contact" refers to the microfluidic module 102 and image sensor 104 abutting (i.e. contacting) each other, being unadhered (i.e. not adhered) to each other and one or both of the microfluidic module 102 and image sensor 104 receiving a force F (see, for example, FIG. 1A) in a direction towards the other of the microfluidic module 102 and image sensor 104. In at least one embodiment, pressure mechanism 107 (e.g. glass slides 108 and 109) presses microfluidic channel 102 and/or image sensor 104 with enough force that the portion of the microfluidic module 102 that defines lower surface 111 of the microfluidic channel 103 and lower surface 118 of microfluidic module 102 removably adheres to the upper surface 120 of the image sensor 104. In at least one embodiment, pressure mechanism 107 provides for no air bubbles to be present at an interface between upper surface 120 of image sensor 104 and lower surface 118 of microfluidic module 102. In at least one embodiment, pressure mechanism 107, as opposed to irreversibly connecting the image sensor 104 and the microfluidic module 102 to each other, provides for changing or replacing microfluidic module 102 (e.g. as a consumable for use with, for example, each fluid sample) and reusing other components of the system (such as but not limited to the light source, image sensor and camera).

In at least one embodiment, one or more fasteners (e.g. pieces of electrical tape or one or more screws) may be placed on microfluidic module 102 and/or image sensor 104 to provide a force to microfluidic module 102 and/or image sensor 104. For example, one or more fasteners (e.g. tape or screws) may be placed the underneath the inlet 114 and/or outlet 116 of microfluidic channel 102 to inhibit tubing, or any other structure providing the fluid sample to the microfluidic channel 102, or any pressure therefrom, from breaking the film forming the lower surface of the microfluidic channel 102.

In at least one embodiment, image sensor 104 is positioned in an image sensor module 122. In at least one embodiment, image sensor module 122 includes a cavity 123 that is sized and shaped to hold (e.g. retain) image sensor 104 in place. In at least one embodiment, image sensor module 122 has an upper surface 124 to support the microfluidic module 102 thereon and provide a flat surface on which the microfluidic module 102 rests. Upper surface 124 is configured to provide for the fluid sample to be level as it flows through the microfluidic channel 103. In at least one embodiment, cavity 123 has a depth that is about equal to a thickness of image sensor 104 so that, when microfluidic module 102 is positioned on top of image sensor module 122, the top surface 120 of the image sensor 104 is equally spaced apart from the bottom surface 111 of the microfluidic channel 103 along a length of the microfluidic channel 103.

Turning to FIG. 1B, illustrated therein is a microfluidic channel 103 is configured to receive a fluid sample containing an analyte of interest for imaging with the image sensor 104. Microfluidic channel 103 is configured to direct the fluid sample over the image sensor 104. In at least one embodiment, the fluid sample is a bodily sample. Any bodily fluids suspected to contain an analyte of interest can be used in conjunction with the system or devices of the invention. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

A bodily fluid may be drawn from a patient and provided to device 100 in a variety of ways, including but not limited to, lancing, injection, or pipetting. In at least one embodiment, a lancet punctures the skin and withdraws a sample using, for example, gravity, capillary action, aspiration, or vacuum force. The lancet may be part of the device, or part of a system, or a stand-alone component. Where needed, the lancet may be activated by a variety of mechanical, electrical, electromechanical, or any other known activation mechanism or any combination of such methods. In another embodiment where no active mechanism is required, a patient can simply provide a bodily fluid to the device, as for example, could occur with a saliva sample or a urine sample. The collected fluid can be placed in a sample collection unit (not shown) within the device 100.

In the embodiment shown in FIG. 1A, microfluidic module 102 is made of a polymeric material, such as but not limited to polydimethyl siloxane (PDMS). Microfluidic module 102 defines at least a portion of microfluidic channel 103. Referring to FIGS. 1A and 1B, microfluidic channel 103 is defined by an upper surface 110, a lower surface 111 and opposed side surfaces 112, 113. In at least one embodiment, microfluidic channel 103 has a width of about 1 mm and a height of about 80 µm. Microfluidic channel 103 has an inlet 114 and an outlet 116.

In at least one embodiment, the lower surface 111 of microfluidic channel 103 is defined by a thin film of a polymeric material, such as but not limited to PDMS, and is positioned above image sensor 104. In at least one embodiment, the upper surface 110 of microfluidic channel 103 and the opposed side surfaces 112,113 of microfluidic channel 103 can be formed as part of microfluidic module 102 and be integral with each other. In at least one embodiment, lower surface 111 of microfluidic channel 103 can be an upper surface of a lower layer of the microfluidic module 102 that is formed separately from an upper layer of the microfluidic module 102. The upper layer of the microfluidic module 102 may define the upper and opposed side surfaces of the microfluidic channel 103. In at least one embodiment, the upper layer and the lower layer can then be bonded together, such as but not limited to by plasma bonding. In at least one embodiment, the lower layer of the microfluidic module 102 may be provided as a spin coated thin film of PDMS, for example having a thickness less than about 20 µm, or of about 20 µm, or in a range of about 15 µm or about 20 µm.

In at least one embodiment, microfluidic module 102, including but not limited to lower layer of microfluidic module 102 defining both lower surface 111 of the microfluidic channel 103 and lower surface 118 of microfluidic module 102, removably abuts upper surface 120 of the image sensor 104. In at least one embodiment, the portion of the microfluidic module 102 defining both lower surface 111 of the microfluidic channel 103 and lower surface 118 of microfluidic module 102 (e.g. the lower layer) has a thickness of about 20 µm and microfluidic channel 103 has a height of about 80 µm, which provides for a sensor-to-analyte distance within a range of about 20 µm to about 100 µm. In at least one embodiment, the portion of the microfluidic module 102 defining both lower surface 111 of the microfluidic channel 103 and lower surface 118 of microfluidic module 102 (e.g. the lower layer) may have a thickness greater than 20 µm and microfluidic channel 103 may have a height greater than 80 µm.

In at least one embodiment, lower surface 118 of microfluidic module 102 rests against and/or abuts image sensor 104. In at least one embodiment, lower surface 118 of microfluidic module 102 rests against and/or abuts a top surface 120 of the image sensor 104. In at least one embodiment, lower surface 118 of microfluidic module 102 is unadhered to top surface 120 of image sensor 104 to provide for microfluidic module 102 to be removable from image sensor 104. In at least one embodiment, microfluidic module 102 is positioned between the light source 106 and the image sensor 104.

Image sensor 104 may be any image sensor capable of detecting and conveying information regarding the fluid sample present in the microfluidic channel 102 that is then used to make an image. For example, in at least one embodiment, the image sensor 103 is a low cost, off-the-shelf complementary metal-oxide-semiconductor (CMOS) image sensor (e.g. IMX219PQ, ¼", 3280×2464 8.08M pixels, back-illumination, Sony), with a 1.12 µm pixel size. In at least one embodiment, image sensor 104 may be commercially sold as a part of the Pi v2 camera and controlled by a Raspberry Pi 3 single board computer.

In at least one embodiment, the height of microfluidic channel 103 provides for components in the fluid sample (e.g. urine) to flow through microfluidic channel 103 without causing blockage.

In at least one embodiment, the device 100 includes a light source 106. Light source is configured to illuminate the image sensor 104 by directing light through microfluidic module 102, microfluidic channel 103 and the fluid sample therein. Light source 106 may be any appropriate light source for illuminating image sensor 104. In at least one embodiment, light from light source 106 originates from an incoherent 1W white LED placed 30 cm above the sample. The lamp (003.859.41, Ikea) faces vertically downwards, directly over the image sensor and the diameter of the area of illumination is approximately 30 cm resulting in average intensity of 1.4 mW/cm$^2$.

For imaging, the fluid sample is dispensed through inlet 114 (e.g. from a syringe) and into the microfluidic channel 103. In at least one embodiment, samples are imaged at a frame rate of about 25 fps. Device 100 may comprise, or may be communicatively coupled to, a camera (not shown) having a processor for creating images. In at least one embodiment, the camera can be operated at a frame rate of about 15 fps to achieve a resolution of 2592×1944 pixels, or at a frame rate of up to 90 fps with a field of view (FoV) of 940×480 pixels. In at least one embodiment, the FoV of the image sensor 104 at 25 fps is 2.60 mm$^2$.

In at least one embodiment, microfluidic channel 103 has a 1 mm in diameter and covers an area of about 2.15 mm$^2$. In at least one embodiment, at a channel height of 80 µm, microfluidic channel 103 is able to retain about 0.172 µL over the field of view.

In at least one embodiment, device 100 may be adapted to a channel-free design for the testing of *Escherichia coli* (*E. coli*). In at least one embodiment, 20 µL of *E. coli* was placed between two plastic thin films ~12 µm thick and placed on an image sensor 104. This strategy is similar to wet mount microscopy and can be used to constrain the sample-sensor distance for a higher resolution on the projection imaging device.

Figure 2:
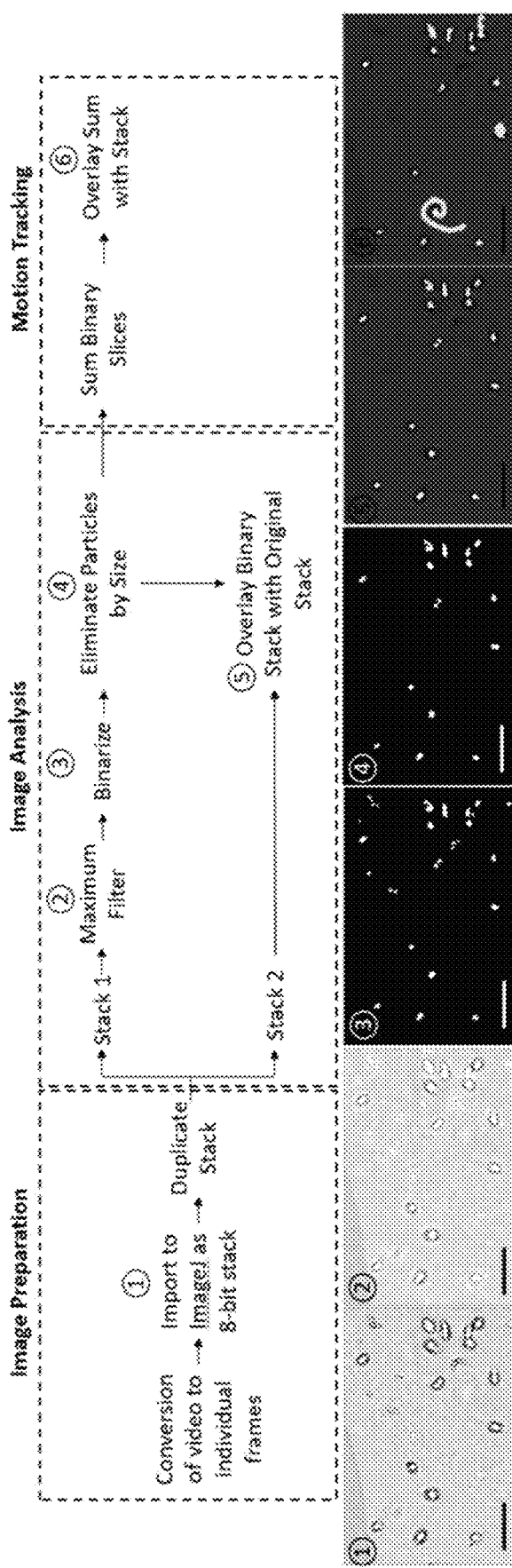
FIG. 2 shows an image processing sequence for the detection of *Trichomonas vaginalis*, according to at least one embodiment described herein.

FIG. 2 depicts an image processing sequence for *Trichomonas vaginalis*, according to at least one embodiment described herein. This sequence identifies the *Trichomonas vaginalis* in the microfluidic channel 103 and highlights its movement across frames. In at least one embodiment, the individual frames of the video are duplicated into two stacks. In Stack 1, each particle (i.e. analyte) in the frames may be identified using a mathematic filter and generate a binary mask. The mask is applied to the original image. These images from multiple frames will be summed together to generate an overlay frame showing the motion path of the particle.

Figure 3A:
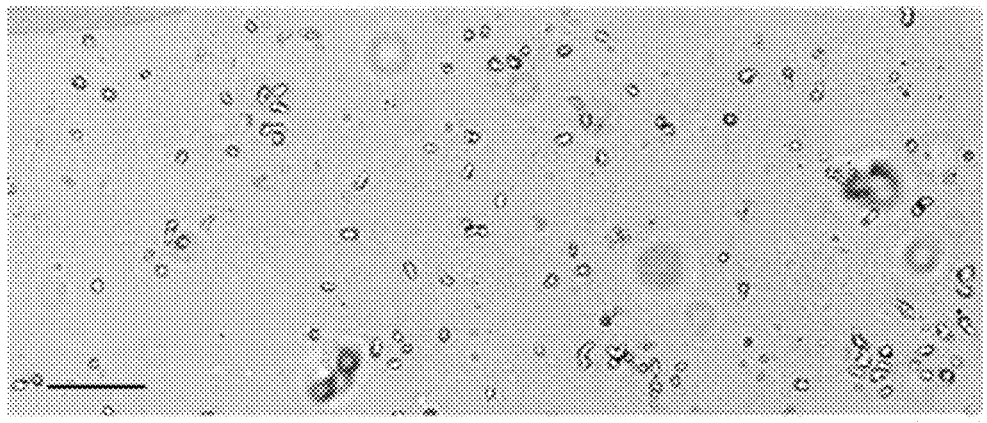
FIG. 3A shows an original image of cultured *Trichomonas vaginalis* in a microfluidic channel an optofluidic imaging device, according to at least one embodiment described herein, at ¼ the field of view.
Figure 3B:
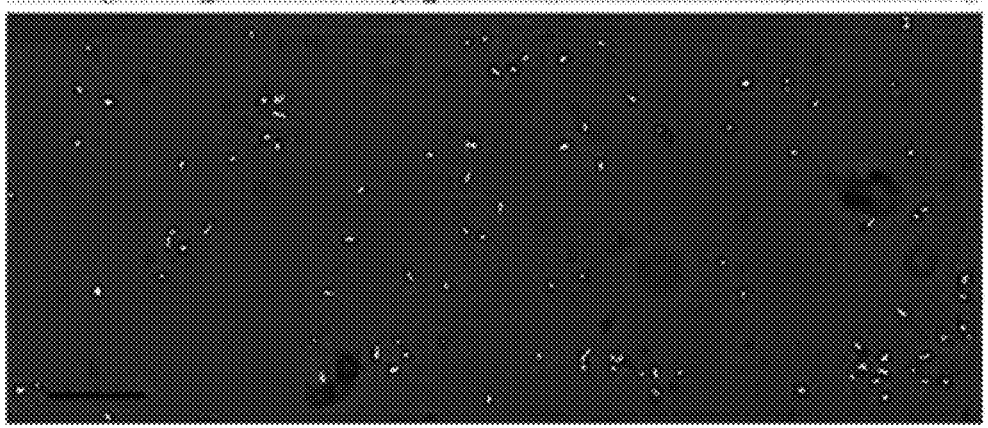
FIG. 3B shows identified *Trichomonas vaginalis* in the image of FIG. 3A post processing.
Figure 3C:
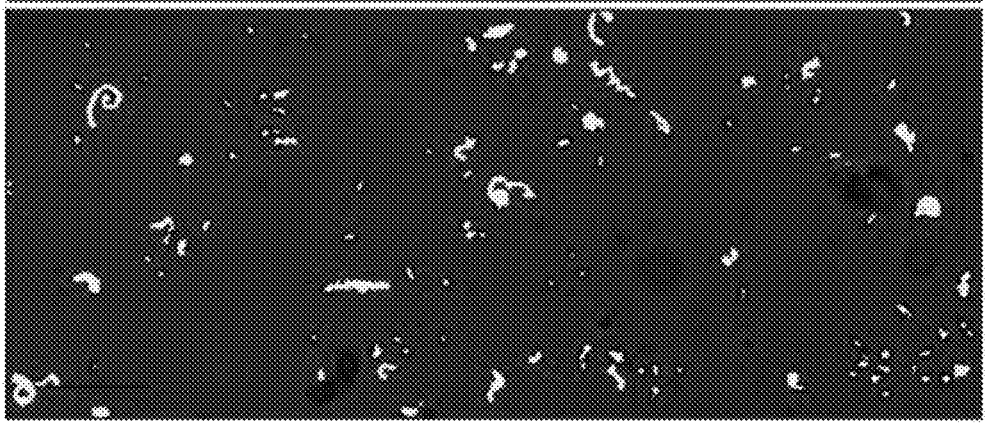
FIG. 3C shows an indicated path of the *Trichomonas vaginalis* moving in the field of view.

FIG. 3 illustrates *Trichomonas vaginalis* identification and movement. FIG. 3A shows an original image of cultured *Trichomonas vaginalis* in the microfluidic channel 103 at ¼ the field of view. *Trichomonas vaginalis* appears elongated with a bright center and dark edges. Three individual *Trichomonas vaginalis* parasites are shown boxed in the images. In FIG. 3B, the lighter portions indicate the identified *Trichomonas vaginalis* in the image post processing. In FIG. 3C, the lighter portions of the image indicate the path of the *Trichomonas vaginalis*. *Trichomonas vaginalis* have a unique locomotion that can be seen when the frames are overlaid. Such unique locomotion pattern can be identified using the overlaid images (e.g., as spiral or corkscrew patterns shown in FIG. 2). Such pattern of movement can be used to uniquely identify the particle or analyte as *Trichomonas vaginalis* for diagnosis purposes. This is also a representation of the viability of the parasites in the fluid sample.

Figure 4:
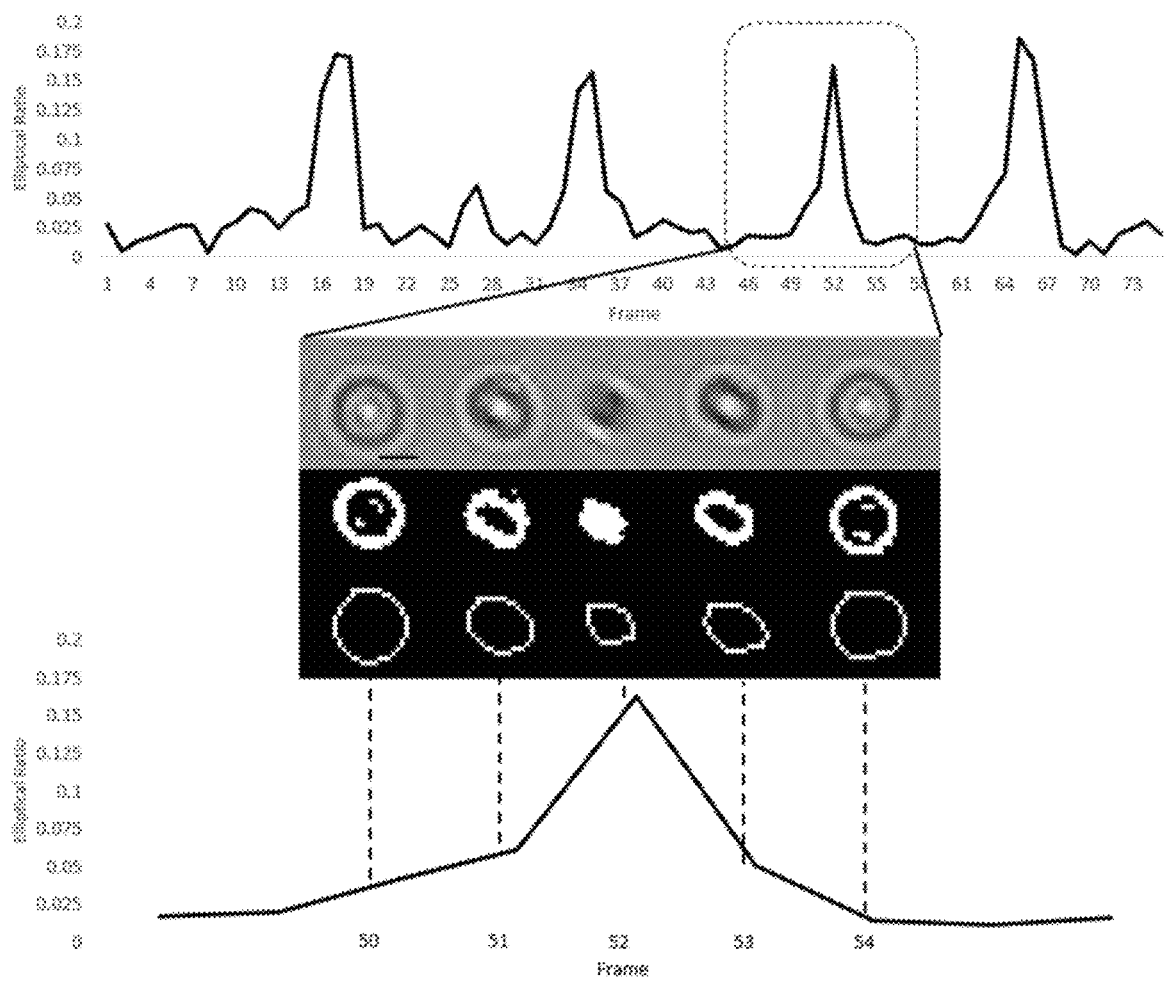
FIG. 4 shows a red blood cell in a urine sample moving through a microfluidics channel in an optofluidic imaging device demonstrating a flipping motion over 70 frames.

FIG. 4 shows a red blood cell (RBC) in a urine sample demonstrating flipping motion over multiple frames. Due to its disk like shape, RBC rolls through the microfluidic channels leaving a shadow changing between a circle and an ellipse. After processing, the frames were made binary and an ellipse was fitted to the image of the RBC to estimate the elliptical ratio of the cell as it flips. This was then graphed against the frame number. A peak in the graph indicates a cell flipping. Again, the flipping pattern measured by the elliptical ratio can be used as a unique marker to identify, for example, RBCs in a fluid sample.

Figure 5:
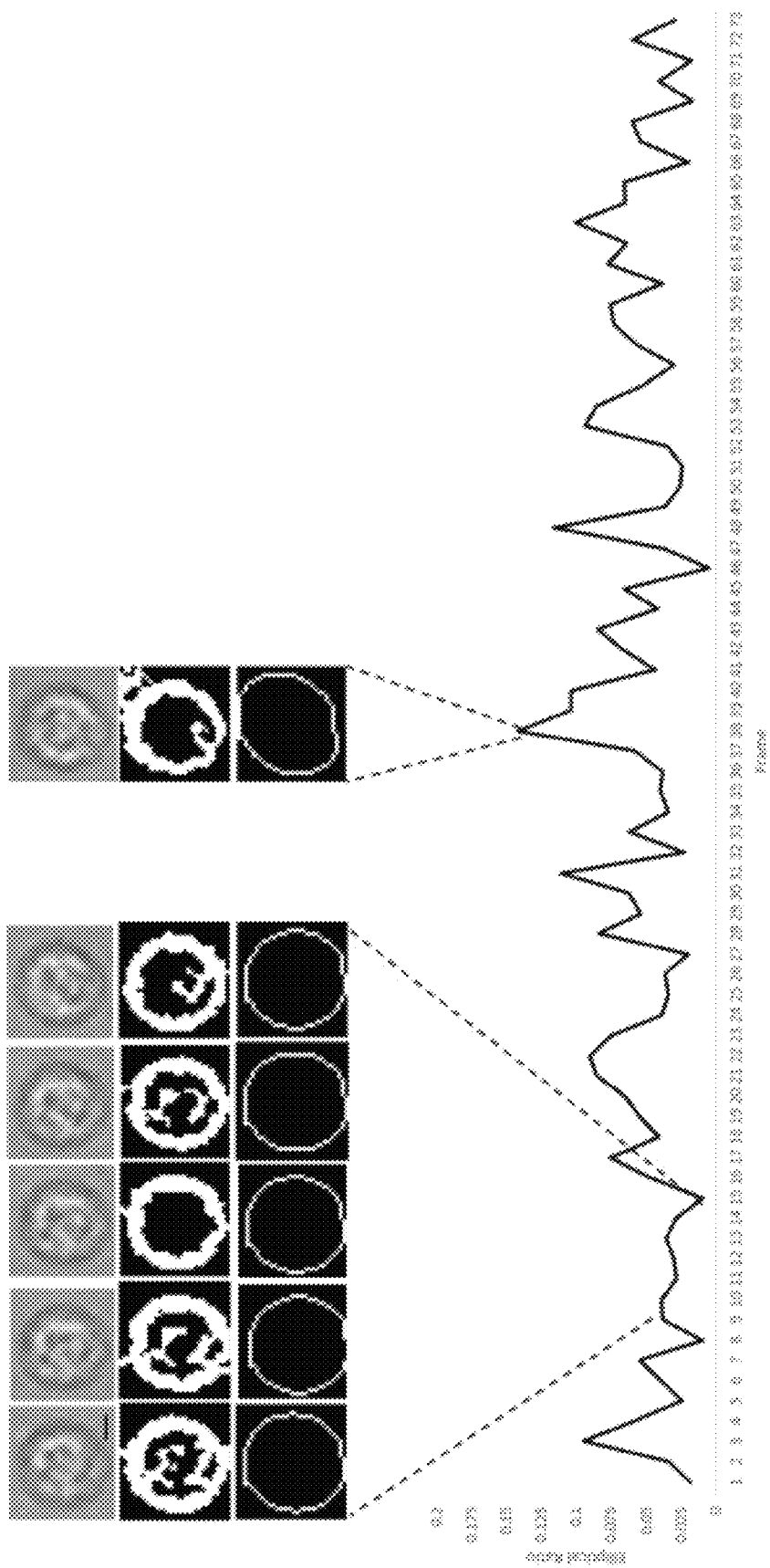
FIG. 5 shows a white blood cell rolling through a microfluidic channel in an optofluidic imaging device, according to at least one embodiment described herein, without a flipping motion.

FIG. 5 depicts a white blood cell rolling through the microfluidic channel 103. Due to the morphology of the white blood cell, typically, they do not flip in the microfluidic channel 103 and thus do not exhibit the same pattern of movement when analyzed based on their major and minor axes. The resulting graph appears random, as there is no flipping of the white blood cell through the microfluidic channel 103. Peaks occasionally arise due to noise in the image that was not eliminated.

Figure 6A:
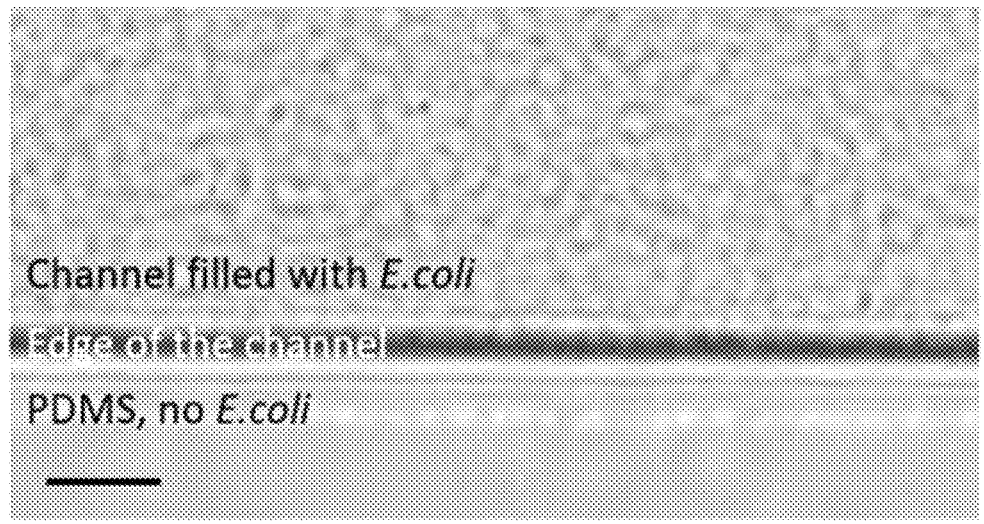
FIG. 6A shows *E. coli* flowing through a microfluidic channel an optofluidic imaging device, according to at least one embodiment described herein.
Figure 6B:
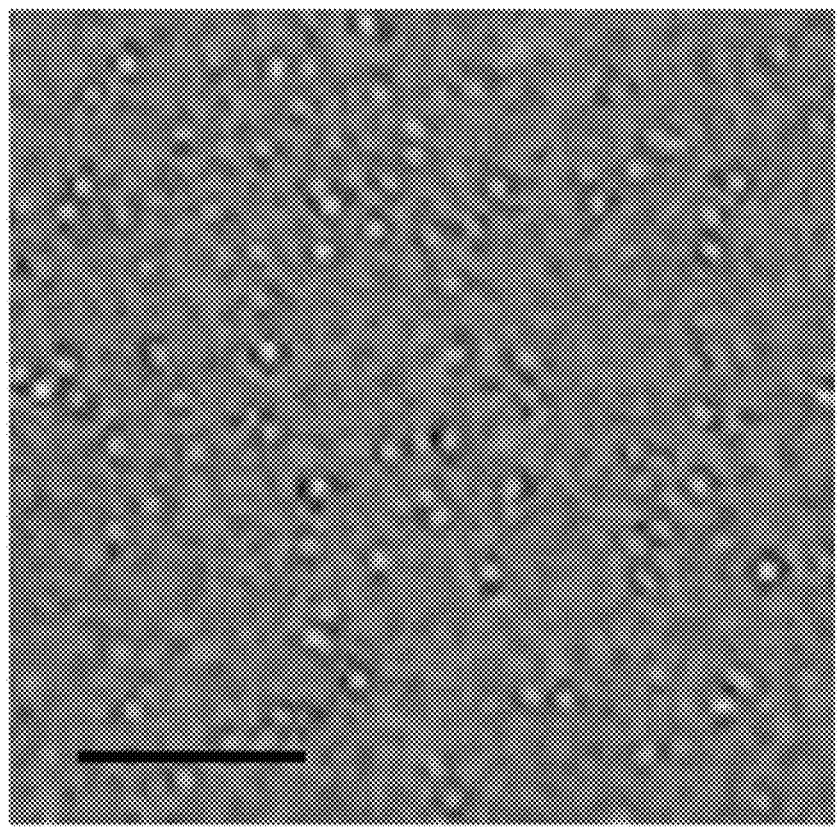
FIG. 6B shows *E. coli* in between a plastic thin film.

FIG. 6A shows *E. coli* flowing through the microfluidic channel 103. At a high concentration, structured noise appears in the microfluidic channel 103 which represents the cultured bacteria. This is seen in contrast with the transparent PDMS channel with nothing in or on it. FIG. 6B shows *E. coli* in between a plastic thin film. The reduced distance between the bacterium and the detector and the group averaging of the frames in the video allows individual bacterium to be resolved.

In at least one embodiment, a method of detecting a presence of an analyte in a fluid sample is described herein. The method includes forming a microfluidic module having a microfluidic channel. In at least one embodiment, the microfluidic module is configured as described above with respect to FIGS. 1A-1C.

In at least one embodiment, the microfluidic module used in the methods described herein has a microfluidic channel having an upper surface, a lower surface and two opposed side surfaces each coupled to and extending between the upper surface and the lower surface. The microfluidic channel is configured to receive the fluid sample at an inlet thereof and direct the fluid sample towards an outlet thereof.

In at least one embodiment, the method also includes positioning an image sensor laterally between the inlet and the outlet of the microfluidic channel. In at least one embodiment, the image sensor is vertically spaced from the microfluidic channel. In at least one embodiment, the image sensor is positioned below a lower surface of the microfluidic channel. In at least one embodiment, the image sensor is communicatively coupled to a processor (e.g. of a camera). In at least one embodiment, the processor is configured to receive signal data from the image sensor.

In at least one embodiment, the method also includes directing a fluid sample, optionally containing the analyte, through the microfluidic channel. For example, the fluid In at least one embodiment, the method also includes directing light from a light source through the fluid sample and towards the image sensor as the fluid sample passes through the microfluidic channel. In at least one embodiment, the image sensor is configured to receive the light after it passes through the fluid sample and output the signal data to the processor.

In at least one embodiment, the processor is configured to detect the presence of the analyte in the fluid sample.

In at least one embodiment, the processor is configured to detect the presence of the analyte in the fluid sample by converting the signal data from the image sensor to image data, creating a video based on the image data and analyzing features of the video to detect the presence of the analyte.

In at least one embodiment, the processor is configured to analyze features of the video by operating a tracking algorithm. The tracking algorithm may provide for identifying and/or indicating (e.g. highlighting) one or more moving particles (e.g. analyte) in the video. The tracking algorithm may track e one or more moving particles in the video as they move across the microfluidic channel. The processor may be configured to extract frames of the particulates to create a new image sequence to be analyzed, for example for the identification and/or detection of a motion biomarker of the analyte. In at least one embodiment, the processor may be configured to compare the tracked movement of one or more moving particles to one or more motion biomarkers (e.g. stored in storage communicatively coupled to the processor). For instance, in at least one embodiment, the processor may be configured to compare the tracked movement of one or more moving particles to one or more motion biomarkers indicating a type of the analyte and/or a state of the analyte (e.g. living, dead, etc.). In at least one embodiment, the processor may be configured to apply a Gaussian mixture-based background/foreground segmentation algorithm and morphological transformations to remove background as well as non-moving objects in the video. In at least one embodiment, edge detection may be used to detect moving objects in each frame of the video. In at least one embodiment, once a particle is detected, both edge detection and a discriminative correlation filter may be used to track the particle over consecutive frames.

In at least one embodiment, the processor is further configured to, based on summing multiple frames of the video, detect the presence of the analyte based on motion-based biomarkers of the analyte.

In at least one embodiment, the analyte is *Trichomonas vaginalis* and the processor is configured to detect the presence of the *Trichomonas vaginalis,* for example based on motion-based biomarkers specific to *Trichomonas vaginalis,* that are for example stored in storage communicatively coupled to the processor.

In at least one embodiment, the analyte may have a non-spherical shape and the processor may be configured to measure an elliptical ratio of shadow images of the analyte over multiple frames of the video to detect the presence of the analyte.

In at least one embodiment, the processor is configured to detect the presence of particles (i.e. analytes or objects) that are smaller than a resolution limit of the system using subpixel motion between frames.

EXAMPLES

A lensless imaging chip based on optical projection has been developed for the purpose of urine analysis. It can identify, for example but not limited to, bacteria, yeast cells, blood cells, parasites, and polystyrene beads. This device may be composed of a light source, an image sensor, and a microfluidic module, as previously described. The microfluidic module with one or more microfluidic channels is integrated with an image sensor by pressurized direct contact. In at least one embodiment, two C-clamps with a glass slide are provided on top of the microfluidics module and a holder is provided below the sensor to provide pressurized direct contact. This "sandwich" configuration involves applying pressure such that the microfluidic channel is pressed onto the sensor. In prior art devices, microfluidic channels are plasma bonded to sensor(s) and cannot be easily removed, meaning the image sensor must be disposable or thoroughly cleaned for repeated use. In at least one embodiment described herein, conformation provides for the image sensor to be reused, which results in a low-cost system.

In at least one embodiment, the sensor is positioned in a sensor holder that includes a divot to hold the sensor in place and support the microfluidic channel by providing a flat surface on top of which the sample is allowed to flow.

In at least one embodiment, a broad-band white light source is placed above the sample. The platform can accommodate a large field of view and sample flow.

In at least one embodiment, the devices and systems described herein provide for analysis of the locomotion of analytes in a fluid sample, such as but not limited to *Trichomonas vaginalis,* in order to identify the analyte. In at least one embodiment, this can be accomplished through non-continuous flow, meaning the flow of the sample through the microfluidic channel is paused intermittently to identify the movement of the analyte (e.g. parasite). In at least one embodiment, the devices and systems described herein provide for analysis of urine samples and for distinguishing different analytes (e.g. pathogens and other components) of the urine sample.

Introduction

Urinalysis is a valuable tool for the diagnosis of various conditions through physical, chemical, and microscopic analysis. Physical analysis is the observation of urine's physical characteristics, whereas chemical and microscopic analysis tests for the presence of chemical analytes [1]-[3] and urine sediments (0.5-500 µm) respectively [4]. Simerville et al. provides a comprehensive list of analytes, sediments, and the current clinical methods of analysis [4].

Generally, in microscopic urinalysis, targeted sediments (listed in Table 1) can be identified through morphological features by a technician after centrifuging the urine to obtain a concentrated sample. In the case of microorganisms, a stain can be used for identification through microscopy, but the gold standard is tissue culture [4]. However, outpatient clinics and even clinical laboratory collection sites do not normally have these specialized instruments or trained technicians to perform these tests. As a result, samples are sent off to a centralized facility for processing, e.g. at the Hamilton Regional Lab Medicine Program, which can have over a thousand samples to process per week. Such processing is efficient for large number of samples, but some issues exist. For example, it is particularly detrimental in the case of trichomoniasis, an infection caused by a parasite known as *Trichomonas vaginalis.* Trichomoniasis is estimated to be the most common non-viral sexually transmitted infection (STI) with 276.4 million cases worldwide [5]. It is often underdiagnosed due to the lack of a conventional test [6] despite being associated with poor birth outcomes [7] such as low birth weight, preterm delivery, and intellectual disability in children [5], [8]. The current gold standard for trichomoniasis diagnosis is culture followed by wet mount microscopy, a procedure not easily done on-site. However, *Trichomonas vaginalis* is only viable for approximately four hours after leaving the body so by the time the samples reach a centralized lab, they may have died. This makes diagnosis more difficult as one of the defining characteristics of *Trichomonas vaginalis* is their unique motility [6]. Point-of-care tests have also been developed for the diagnosis of trichomoniasis, however it remains too costly to implement [9].

Another example of a potential condition is a urinary tract infection (UTI), an infection caused by the presence of bacteria in the urinary tract with prevalence among communities and hospitals. UTIs affect almost 50% of the population at least once in their lifetime, leading to an annual health care cost of approximately $3.5 billion in the US [10], $1.6 billion of which contributes to the administration of antibiotics [11], enhancing the risk of antibiotic resistance [12]. It takes 48 hours for urine to be cultured and 70% of samples come back negative [13]. A third particulate that can be found in urine is red blood cells (RBCs). Blood in the urine is known as hematuria and can be a symptom of a large range of conditions, including kidney disease, cancer, etc. [4] The clinical definition of hematuria is >3 RBCs per high power field meaning each sample must be tested under a microscope by a trained technician, a time consuming and inconvenient process.

To improve the efficacy of urinalysis, flow cytometry techniques have been applied [11] as a preliminary screening tool that aims to reduce the number of samples cultured, reducing the workload, time, and costs in large laboratories [14]. The use of flow cytometry as a pre-screening tool has presented a 28%-60% reduction in the number of cultured samples [11]. In addition to saving cost and resources, by immediately receiving a negative result, physicians avoid prescribing unnecessary antibiotics and can go on to providing a more accurate diagnosis quicker. Savings of $239-$306 USD per 100 samples have also been reported, indicating the use of a flow cytometer is also cost efficient [15]. Nevertheless, flow cytometry has its limitations as the samples must be labelled, and in image-based flow cytometry the specimens are at risk of being imaged out of focus due to a short depth of field [16]. Flow cytometers have a large benchtop footprint and are expensive. Thus, they are typically implemented at the level of the centralized processing facility, which often sees a delay between sample collection and processing due to the transportation of the samples. For the most accurate results, the urine must be examined within two hours as longer delay times often cause unreliable results [4]. A platform that can be integrated into the physician's office would ensure that the sample is processed in real time. The workflow for urinalysis can benefit from a less expensive and more time-efficient diagnostic tool.

Lensless, or lens-free, imaging devices offer a different approach to detecting small particles in large fluid volumes. Lensless microscopy records the image of the sample on the detector without any intervening lenses. Imaging without lenses offers advantages over cell culture and traditional microscopy, including low-cost, large field of view, and portability, which inherently leads to high throughput while maintaining sub-micron resolution. It is particularly well suited to analysis applications in which a large area or volume must be screened in order to determine whether a sample is positive or negative, making it ideal for urine analysis. Lensless imaging can be used in combination with microfluidics to make a cost-effective and portable device that can evaluate milliliters of liquid for microscopic specimen, in under an hour, without the need for centrifugation. Shadow imaging and holographic imaging are two lensless techniques resulting in a bright field image [17]. The resolution of the images attained from these modalities is limited to twice the size of the pixel and depends on the sample-sensor distance [17]. An advantage of shadow imaging is that the images acquired do not require post processing or reconstruction. It is normally well suited for the imaging of biological specimen, in which the samples have some degree of transparency. This paper demonstrates that shadow imaging is well-suited to the application of urine analysis, especially in combination with motion analysis of urine sediments.

The mechanisms of microorganism motility have been explored by the microbiology community [18]. High-resolution conventional microscopy was a key component in understanding of the mechanisms by which microorganisms move by aiding in the study of physiological and biological responses. In contrast, its use as an endogenous biomarker, especially in a high throughput context, has been understudied. There are significant advantages to utilizing the motility of different organisms for identification, especially in urine analysis. In the case of *Trichomonas vaginalis*, motility exhibited through its flagella has been previously described as a corkscrew or zigzag motion [19]. Apart from microorganisms, there have also been extensive studies into the movement of RBCs in flow [20]. Due to the biconcave shape of the cells, they exhibit a flipping motion as they travel through a fluidic channel. This characteristic motion can be exploited for identification in low-resolution settings. There are inherent advantages of microfluidic lensless shadow imaging devices to study the use of motility as a contrast mechanism. For one, there is a large area over which the micro particles are allowed to move as shadow imaging has an inherently large depth of field and field of view. There is little risk of the organism travelling outside an observational area. It is a high-throughput system in which many particles can be tracked simultaneously; and the low resolution makes it necessary for motility to be a distinguishing feature. Microfluidic control allows for testing in pulsed flow to determine whether the particulates exhibit distinguishing features in still or moving flow. Finally, in contrast with holographic imaging, no image reconstruction in required.

This application presents the development of a low-cost lab-on-chip lensless optofluidic technology for the rapid point-of-care detection of urinary constituents. This technique utilizes the motion of fluid (e.g. urinary) components as a biomarker and endogenous contrast mechanism, bypassing the need for the addition of molecular biomarkers or any sample preparation. In addition, such motion-based biomarker also circumvents the need for a high-resolution imaging modality, as the motion characteristics of the specimen can be analyzed easily in a low-resolution context. Certain components, like *Trichomonas vaginalis*, are self-propelled parasites that have their own inherent characteristic motility through the movement of their flagella, and others, like red blood cells, have their own distinct movement due to the flow in the channel. Shadow imaging provides a large field of view, which allows for the detection of rare events as the urine flows over the detector.

By filtering out negative samples early from the screening process, unnecessary culturing is avoided, as well as the potential pre-emptive prescribing of antibiotics. Ideally, this device would be implemented as a point-of-care device in clinics to reduce the number of samples being sent to the lab, as well as allowing for personalized medicine.

Materials and Methods

In this platform, a fluid sample was flowed within a microfluidic channel directly over a CMOS image sensor, which captured a series of projection images. It was then processed with an automated detection algorithm.

Device Design and Fabrication

As shown in FIGS. 1A-1C, the lensless optofluidic shadow imaging device consists of a polydimethyl-siloxane (PDMS) microfluidic channel of 1 mm width and 80 µm height, with an inlet and outlet hole, bonded to a spin coated thin film PDMS, 15 pm in thickness. This channel is clamped to a low cost complementary metal-oxide-semiconductor (CMOS) image sensor (IMX219PQ, ¼", 3280×2464 8.08M pixels, back-illumination, Sony), with a 1.12 µm pixel size. The image sensor is commercially sold as a part of the Pi v2 camera and is controlled by a Raspberry Pi 3 single board computer. The clamping system, as opposed to bonding the microfluidic module to the image sensor, provides for the image sensor to be reusable as the channel can easily be switched out. Pieces of electrical tape are placed underneath the inlet and outlet holes to inhibit the tubing, or any pressure, from breaking the film. The channel height provides for all components in the fluid (e.g. urine) sample to flow through the channel without causing blockage. The light source illuminating the platform originates from an incoherent 1 W white LED placed 30 cm above the sample. The lamp (003.859.41, Ikea) faces vertically downwards, directly over the image sensor and the diameter of the area of illumination is approximately 30 cm resulting in average intensity of 1.4 mW/cm$^2$. For imaging, a liquid sample is dispensed from a syringe and into the microfluidic channel. Samples were typically imaged at a frame rate of 25 fps. The camera can be operated at a slower frame rate of 15 fps in order to achieve a resolution of 2592×1944 pixels, or at a faster frame rate of up to 90 fps with a field of view (FoV) of 940×480 pixels. The FoV of the sensor at 25fps is 2.60 mm$^2$. The flow channel, which is 1 mm in diameter, covers an area of 2.15 mm$^2$. At a channel height of 80 µm, it is able to hold 0.172 µl over the field of view. The optofluidic microscope integrates microscale fluidics and optics in a single system to detect the different components of urine without pre-processing of the sample.

The device was also adapted to a channel-free design for the testing of *Escherichia coli* (*E. coli*). 20 µl of *E. coli* was placed between two plastic thin films ~12 µm thick and placed on the imager. This strategy is similar to wet mount microscopy and can be used to constrain the sample-sensor distance for a higher resolution on the projection imaging device.

Biological Sample Preparation and Measurements

In order to identify the different components in urine, three homogenous samples were tested: whole blood, *Trichomonas vaginalis*, *E. coli* (*E. coli* strain pMS201). *Trichomonas vaginalis* was cultured from a patient in modified Diamonds medium. *E. coli* was cultured in (LB) media.

Whole blood samples were diluted by a factor of 1:100 in 1× phosphate-buffered saline (PBS) pH 7. Cultured *Trichomonas vaginalis* was injected into the channel with no prior preparation. The *E. coli* sample was grown in Luria-Bertani media overnight and was allowed to reach a concentration of 108 CFU/mL The samples were then manually injected into the microfluidic channel under white-light illumination. Images of the blood cells are captured by the image sensor. The whole blood and *E. coli* samples were manually injected with a syringe and travelled at a rate of 500 μm/sec. *Trichomonas vaginalis* was injected into the channel and allowed to rest without flow in order to analyze the locomotion of individual parasites.

Image Processing

In order to identify the urinary constituents in the acquired image sequences, a tracking algorithm was developed to highlight each moving particle in the video. Once each moving object is identified, they are tracked as they move across the channel. The frames of the particulates are then extracted to create a new image sequence to be analyzed for a motion biomarker. Once the particulate matches a motion biomarker, it can be properly classified.

Tracking

The tracking algorithm was developed in Python with the OpenCV image processing package to highlight each moving particle in the video. The developed algorithm applies the Gaussian mixture-based background/foreground segmentation algorithm and morphological transformations to remove background as well as non-moving objects in the video [21]. Edge detection is then used to detect moving objects in each frame. Once a particle is detected, both edge detection and the discriminative correlation filter are used to track it over consecutive frames. The Kalman filter is used to predict the position of particles if overlapping were to occur.

*Trichomonas vaginalis*

FIG. 2 outlines image processing flow for *Trichomonas vaginalis* in Fiji/ImageJ (v1.52i) [22], [23]. After using FFmpeg [24] to convert the video to individual frames, a maximum filter was used to enhance the brightness of the center of the parasites. The images were then binarized and white areas smaller than 20 pixels were eliminated as this is not representative of the size of *Trichomonas vaginalis*. This new stack can be overlaid with the original image stack to identify the parasites. It can also be summed together for motion analysis.

Blood Cells

In order to determine whether this signature exists in RBCs present in urine, urine samples from the HGH microbiology lab positive for hematuria were tested. Urine samples positive for RBCs were flown through the channel without preprocessing and RBCs were tracked and identified based on their rotational pattern. A stack of images following an RBC travelling through the channel was analyzed using ImageJ. The stack was averaged, and the averaged frame was subtracted from the stack to remove background noise. The stack was then converted to binary. Using the built-in Analyze Particles tool in ImageJ [22], [23], anything appearing in the frame stack that was smaller than 20 pixels was eliminated. The major and minor axis of the cell as it travelled through the channel was extracted and the elliptical ratio was defined using Eq. 1. The same process was done for WBCs.

The major and minor axis of the ellipse were extrapolated from each cell. It is important to note that the eccentricity of the cells themselves remain the same, but the shadow projected onto the detector can be analyzed by tracking and comparing the changes between the major and minor axis. The elliptical ratio of the RBC's shadow image is defined in Equation 1 to capture the difference of major axis to minor axis in the shadow image:

$$\text{Elliptical Ratio} = (\text{Major Axis} - \text{Minor Axis})/(\text{Major Axis} + \text{Minor Axis}) \quad (1)$$

*Escherichia coli*

In the case of *E. coli*, a stack of frames from the channel-free device was averaged and subtracted from the stack. Groups of three images were averaged in the stack to give a clearer image of the bacteria.

Results

Lensless Optofluidic Device

Typically, in an optofluidic projection imaging device, a microfluidic channel is bonded to an image sensor, and an incoherent light source, typically an LED, is placed above the senor. Samples are flown through the channel, in contact with the image sensor. In order to reduce the wear on the sensor and avoid cross contamination, this design features a removable flow channel module separate from the image sensor. The flow channel was clamped to the image sensor with a pressure-coupling mechanism, which also provided stability (see FIG. 1C). Microfluidic channels of varying heights were fabricated and tested, and a channel height of 80 μm was identified to be optimal. It allowed for the passing of all urinary constituents in the tested samples, without blockage. It also allowed sufficient resolution to identify the particulates within urine with the application of motion biomarkers. For the channel to be a self-contained replaceable module, it was bonded to a PDMS thin film 15 μm in thickness before being clamped to the sensor. The reduction in resolution due to the presence of the thin film beneath the microfluidic channel is not enough to render the algorithm unable to identify the particles. This channel is clamped to a low-cost, off-the-shelf, complementary metal-oxide-semiconductor (CMOS) image sensor with a 1.12 μm pixel size at a frame rate of 25 fps over a field of view of 2.60 mm$^2$. The channel fills the entire length of the sensor and 1 mm of its width, covering an active pixel area of 2.20 mm$^2$. The illumination is provided by a broadband LED.

Image and Video Processing

The tracking algorithm identifies each moving particle in the video, then tracks them as they move across the channel. The results are shown in FIG. 3. Once the particles are tracked throughout the video, the frames of the particulates can be extracted from within the bounding boxes to create a new image sequence to be analyzed for a motion biomarker. Herein, such motion biomarkers can be used to classify red and white blood cells and *Trichomonas vaginalis*.

*Trichomonas vaginalis*

Positive control of cultured *Trichomonas vaginalis* was measured to validate the appearance of the parasite on the optofluidic microscope. The parasites are oblong in shape and can be up to 20 μm in length, which can be seen in FIG. 4A. On the lensless imaging platform, the parasites appear bright in the center due to the lensing effect of the parasites themselves, which focuses the incident light onto the detector. Similar effects have been seen in cyanobacteria as a mechanism to sense light direction [25]. When compared to other urine sediments, like bacteria and RBCs, *Trichomonas vaginalis* is distinctly different due to its oblong shape and bright center. The closest particle in size is the WBC, which have nuclei that cast shadows at the center of the cell, and it is more spherical. The bright centers of the parasites as well as their large size and defined edges was the first defining feature used to identify them among the other particles present in the media. With this method, all particles that are the same size as *Trichomonas vaginalis* with a bright center will be identified (FIG. 4*b*). While this is a sensitive method, it is not specific as *Trichomonas vaginalis* detection is difficult in still images in which motility patterns are not visible [6].

In clinical practice, morphology as well as the inherent locomotion of the parasites are used as identifiers in bright-field microscopy [6]. Characteristic *Trichomonas vaginalis* motility was confirmed independently by an experienced laboratory technologist. To recognize this type of motion, 200 frames of images were summed over 8 seconds of movement. Once summed, their movement pattern can be recognized. Some parasites moved in a zig-zag pattern, others in corkscrew patterns, as shown in the image (FIG. 4C). This is a distinctive identifier for *Trichomonas vaginalis*. Other particles in a paused fluid would not have a motility pattern similar to that of this parasite.

Similar results were found when a urine sample was spiked with *Trichomonas vaginalis*. A true positive urine sample with *Trichomonas vaginalis* was unattainable as the parasites normally die within hours of sample collection.

Blood Cells

In order to identify the different components in urine, homogenous samples were first tested. The whole blood samples were diluted in 1× PBS pH 7 and flowed through the channel (see FIG. 5). Some red blood cells (RBCs) are distinguishable through morphological features, particularly a divot in the center of the cell, which appears as a shadow. The biconcave shape of the RBCs and the laminar parabolic flow of the fluid through the channel causes the RBCs to flip repeatedly as they travel through the channel, as opposed to the rolling observed from other particles. Due to this motion, the RBCs do not appear to have this unique morphology in every frame. In some frames, the RBCs appear to be linear in shape as seen in FIG. 5. In order to identify and accurately count the RBCs in their flow, tracking and motion identification methods are employed.

Urine samples from the HGH microbiology lab positive for hematuria were tested. Urine samples positive for RBCs were flown through the channel without preprocessing and RBCs were tracked and identified based on their rotational pattern. Background in these images was removed first, then an ellipse was fitted around the RBC. The major and minor axis of the ellipse were extrapolated from each cell, which is defined as the elliptical ratio of the RBC's shadow image. The elliptical ration was then plotted as a function of frame number in FIG. 6.

The peaks indicate when the cell flips in the channel. When contrasted against white blood cells that roll through the channel, the same distinct pattern of peaks is not seen. The WBCs were analyzed with the same algorithm as the RBCs. The only difference in the algorithm is that, with the WBCs, anything appearing in the stack that was smaller than 50 pixels was eliminated. This is due to the size difference between the WBCs and RBCs.

Although RBCs are normally reported to be around 6-8 µm in diameter, the RBCs in an 80 µm channel appeared to be around 15 µm. The shadows are enlarged due to the height of the channel and the position of the objects within the channel. The further away the sample is from the sensor, the larger and less clear the sample appears. The WBCs are also enlarged, as they appear to be around 30 µm as opposed to the reported 12-17 µm. This discrepancy between the real size and morphology of the cells versus how they appear on the detector indicate that it is not a reliable method of identification. By analyzing and applying the flipping motion of the cells, a more differentiable characterization can be executed.

In addition, the flow of the particles through the channel is not uniform. Due to the laminar parabolic flow in the channel, the particles exhibit a different flow speed based on their position in the channel. The image size and the flow speed of objects in the images can be used to calculate the actual size and height of the particle [26]. The number of blood cells in urine can be counted without sample preparation, however as there is a much higher concentration of blood cells in blood and the blood sample must be diluted if this platform should be extended to hemocytometry.

*Escherichia Coli*

*E. coli* (strain pMS201) was also measured using the lensless imager. Bacteria are small, ~1 µm in diameter, and highly transparent. This makes imaging on a lensless microscope challenging, given that the pixel size is usually a few micrometers. Normally, *E. coli* is stained prior to imaging on a bright-field microscope. It was determined that at a high concentration of 109 CFU/ml, the bacteria are very evident in the channel. However, individual bacteria are impossible to differentiate using these images even at this concentration. The same was seen in urine samples positive for bacteria in amounts greater than 100 CFU/ml. In a urine sample positive for bacteria at a concentration of >100 CFU/ml, the bacteria is not visible in a single frame. When seen in a video, the bacteria resemble a noisy background and individual bacteria are difficult to examine. In order to increase the resolution of the system, a channel-free design was employed.

Channel-Free Design

In the channel-free design, the microfluidic channel was replaced with two plastic thin films, between which 20 µm of *E. coli* was added. In order to make the appearance of *E. coli* more evident, a simple algorithm that averages the frames in a stack in groups of three was employed. This processing worked due to the slow movement of the cells on the plastic thin film, and because the subcellular feature of bacteria was not needed for this application.

Discussion and Conclusion

Herein, a reusable, lensless imaging platform for the clinical analysis of urine samples is described. Shadow imaging, in combination with motion analysis as an endogenous biomarker, leads to a unique application. This device demonstrates effective detection of analytes (e.g. blood cells and parasites) directly in fluid (e.g. urine) samples without the need for concentration or culture. In one example, *Trichomonas vaginalis* self-propel through the movement of their flagella, often resulting in a corkscrew or zig-zag movement. In another example, RBCs have a distinct flipping movement due to the flow in the microfluidic channel and their biconcave morphology. In this context, shadow imaging may take advantage of this unique motility for particle identification.

An important advantage of shadow imaging is that the images acquired do not require extensive post processing or reconstruction. It is normally well suited for the imaging of biological specimen, in which the samples have some degree of transparency. Recently, holographic imaging is a popular lensless imaging technique where a diffraction image is projected onto the sensor. Although holographic imaging has the advantage of reconstructing different planes in a 3D volume, it has challenges in real time imaging of a deep (~50-100 µm) microfluidic flow channel due to the lengthy processing time. Herein it is demonstrated that shadow imaging has the specific advantage of being able to be used in combination with motility biomarkers to specifically identify urine sediments.

In terms of the lensless imaging device design, the use of a clamping system may provide for replacement of microfluidic channels between samples without having to replace the image sensor. Disposable sample holders may be important in clinical use to mitigate cross-contamination. Typically, a PDMS microfluidic channel is adhered to the sensor through plasma bonding to ensure a minimal sample-sensor distance and high resolution. In prior art devices, the microfluidic channel and the imager need to be replaced after each test, significantly increasing the cost. In addition, in typical shadow imaging devices, the height of the device is often constrained to the size of the particles to ensure that they remain close to the sensor as they flow through the channel. Due to the nature of urine, a fluid sample with a large diversity of constituents in both size and shape, a channel should be fabricated such that the largest of particles can pass through. Although the resolution of particles is best when the sample-sensor distance is highly reduced, herein is it shown that a image sensor to sample fluid distance of about 20 µm, or less, to about 100 µm does not negatively affect particle identification. The image sensor, with a pixel size 1.12 µm, for example, provides for a relatively high resolution in the context of shadow-imaging devices. The use of a microfluidic channel may provide for continuously screening for pathogens in the fluid sample. In at least one embodiment, when having a height of 80 µm, the microfluidic channel may hold 0.172 µL over the field of view of ~2.15 mm². This height provides for all of the components of urine and blood to pass through without issue and retains the resolution necessary to identify the pathogens. Reconstruction of the images is not necessary, and a sufficient resolution is achieved for the identification of the components. Furthermore, the use of a Raspberry Pi microcontroller and associated camera significantly simplified the integrated device and greatly reduced the total system cost to an amount that may be suitable for applications in low resource areas.

Herein, a tracking algorithm is disclosed to identify objects in the microfluidic channel. Once each object is identified, a video of its movement with the flow is used in the motion analysis.

To classify each particle, distinguishing features must be used. In at least one embodiment, the morphology of different cells is an identifying feature that can be used to distinguish one from another. However, on an imaging platform with a lower resolution, the morphology alone may not be enough to distinguish different particulates [28]. RBCs in whole blood and found natively in urine illustrates the flipping motion characterized extensively in prior work [20]. By analyzing the flipping of the cells in the channel, an algorithm has been developed for automatic detection. The elliptical ratio of the RBCs, as they flip through the channel, is distinct from that of the WBCs, indicating a unique biomarker.

Herein it is demonstrated that *Trichomonas vaginalis* can be identified based on its size and bright center. Motion analysis arises through frame accumulation, in which the unique corkscrew motion, a measure of viability can be seen, which is similar to what others have reported for other motile parasites [29]. Increasing the amount of urine being screened on the device increases the limit of detection. Trichomoniasis is typically diagnosed through wet mount microscopy where anywhere between <1 and 16 parasites can be found per high power field of 60× [4]. The field of view of a 60× image can be approximated to be 0.03 mm², which is far less than the field of view of the presented microscope (2.6 mm²). It is likely that very low amounts of *Trichomonas vaginalis* can be detected with this platform as there are continuous flow of the samples and the parasite is fairly large and distinguishable. In addition, due to the low-cost of the system, it is implementable at the site of sample collection. This gives us the opportunity to analyze the motion of the parasite when it is at its liveliest.

Optically identifying free-floating bacteria is challenging. Most bacteria are ~1 µm in size and transparent. When placed between two plastic thin films, the bacteria are close to the sensor and move very slowly (e.g. relative to other particles/analytes). The frames in this video can be averaged to recover the presence of *E. coli*. For example, in a urine sample flowing through a microfluidic channel that has an abundance of bacteria, there is a visible distortion in the video, likened to structured noise In at least one embodiment, crystals and casts are large and identifiable based on their morphology. These characteristics may be used to train an algorithm to automatically identify the specimen. In at least one embodiment, a diagnosis tool is described that uses identifiable characteristics of each component of a fluid sample to analyze each component rapidly and accurately.

Herein, it is demonstrated that lensless optofluidic projection imaging is able to simultaneously detect various pathogens in a fluid sample (e.g. urine). The implementation of a fully automated lensless imaging platform can quickly eliminate negative samples from further processing to significantly reduce costs; and administer earlier and more appropriate treatments. Such features fit the application of point-of-care diagnosis in hospitals, clinics and long term care facilities.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

[1] C.-C. Lin, C.-C. Tseng, T.-K. Chuang, D.-S. Lee, and G.-B. Lee,
"Urine analysis in microfluidic devices.," Analyst, vol. 136, no. 13, pp. 2669-88, July 2011.

[2] R. N. Goyal, S. Bishnoi, and B. Agrawal, "Electrochemical sensor for the simultaneous determination of caffeine and aspirin in human urine samples," J. Electroanal. Chem., vol. 655, no. 2, pp. 97-102, June 2011.

[3] B. Kuswandi, Nuriman, J. Huskens, and W. Verboom, "Optical sensing systems for microfluidic devices: A review," Anal. Chim. Acta, vol. 601, no. 2, pp. 141-155, October 2007.

[4] J. A. Simerville, W. C. Maxted, and J. J. Pahira, "Urinalysis: a comprehensive review.," Am. Fam. Physician, vol. 71, no. 6, pp. 1153-62, March 2005.

[5] P. Kissinger, "*Trichomonas vaginalis:* a review of epidemiologic, clinical and treatment issues," BMC Infect. Dis., vol. 15, no. 1, p. 307, December 2015.

[6] G. E. Garber, "The laboratory diagnosis of *Trichomonas vaginalis.*," Can. J. Infect. Dis. Med. Microbiol.=J. Can. des Mal. Infect. la Microbiol. medicale, vol. 16, no. 1, pp. 35-8, January 2005.

[7] B. J. Silver, R. J. Guy, J. M. Kaldor, M. S. Jamil, and A. R. Rumbold, "*Trichomonas vaginalis* as a Cause of Perinatal Morbidity," Sex. Transm. Dis., vol. 41, no. 6, pp. 369-376, June 2014.

[8] J. R. Mann, S. McDermott, T. L. Barnes, J. Hardin, H. Bao, and L. Zhou, "Trichomoniasis in Pregnancy and Mental Retardation in Children," Ann. Epidemiol., vol. 19, no. 12, pp. 891-899, December 2009.

[9] C. A. Gaydos, J. D. Klausner, N. P. Pai, H. Kelly, C. Coltart, and R. W. Peeling, "Rapid and point-of-care tests for the diagnosis of Trichomonas vaginalis in women and men.," Sex. Transm. Infect., vol. 93, no. S4, pp. S31-S35, December 2017.

[10] M. Davenport, K. E. Mach, L. M. D. Shortliffe, N. Banaei, T.-H. Wang, and J. C. Liao, "New and developing diagnostic technologies for urinary tract infections," Nat. Rev. Urol., vol. 14, no. 5, pp. 296-310, May 2017.

[11] P. Mejuto, M. Luengo, and J. Diaz-Gigante, "Automated Flow Cytometry: An Alternative to Urine Culture in a Routine Clinical Microbiology Laboratory?," Int. J. Microbiol., vol. 2017, pp. 1-8, September 2017.

[12] A. Sorlozano et al., "Evolution of the resistance to antibiotics of bacteria involved in urinary tract infections: A 7-year surveillance study," Am. J. Infect. Control, vol. 42, no. 10, pp. 1033-1038, October 2014.

[13] M. A. C. Broeren, S. Bahceci, H. L. Vader, and N. L. A. Arents, "Screening for urinary tract infection with the Sysmex UF-1000i urine flow cytometer.," J. Clin. Microbiol., vol. 49, no. 3, pp. 1025-9, March 2011.

[14] W. J. Mcisaac, D. E. Low, A. Biringer, N. Pimlott, M. Evans, and R. Glazier, "The impact of empirical management of acute cystitis on unnecessary antibiotic use.," Arch. Intern. Med., vol. 162, no. 5, pp. 600-5, March 2002.

[15] K. Yasuma et al., "Evaluation of a UF-1000i screening method to identify the bacteriuria for cultures and susceptibility testing," Rinsho Byori., vol. 60, no. 11, pp. 1070-4, November 2012.

[16] J. Delanghe, "New Screening Diagnostic Techniques In Urinalysis," Acta Clin. Belg., vol. 62, no. 3, pp. 155-161, June 2007.

[17] A. Ozcan and E. McLeod, "Lensless Imaging and Sensing," Annu. Rev. Biomed. Eng., vol. 18, no. 1, pp. 77-102, July 2016.

[18] K. L. Hill, "Parasites in motion: flagellum-driven cell motility in African trypanosomes," Curr. Opin. Microbiol., vol. 13, no. 4, pp. 459-465, August 2010.

[19] J. Huppert, J. Mortensen, J. Reed, J. Kahn, W. Miller, and M. Hobbs, "6: Comparison of diagnostic methods for Trichomonas vaginalis," J. Adolesc. Heal., vol. 40, no. 2, p. S8, February 2007.

[20] J. Dupire, M. Socol, and A. Viallat, "Full dynamics of a red blood cell in shear flow.," Proc. Natl. Acad. Sci. U. S. A., vol. 109, no. 51, pp. 20808-13, December 2012.

[21] Z. Zivkovic, "Improved Adaptive Gaussian Mixture Model for Background Subtraction," 2004.

[22] J. Schindelin et al., "Fiji: an open-source platform for biological-image analysis," Nat. Methods, vol. 9, no. 7, pp. 676-682, July 2012.

[23] J. Schindelin, C. T. Rueden, M. C. Hiner, and K. W. Eliceiri, "The ImageJ ecosystem: An open platform for biomedical image analysis," Mol. Reprod. Dev., vol. 82, no. 7-8, pp. 518-529, July 2015.

[24] FFmpeg Developers, "FFmpeg Tool (V.4.2)." 2019.

[25] N. Schuergers et al., "Cyanobacteria use micro-optics to sense light direction.," Elife, vol. 5, February 2016.

[26] A. Shanmugam and C. Salthouse, "Lensless fluorescence imaging with height calculation," J. Biomed. Opt., vol. 19, no. 1, p. 016002, January 2014.

[27] S. Ji, W. Xu, M. Yang, and K. Yu, "3D Convolutional Neural Networks for Human Action Recognition," IEEE Trans. Pattern Anal. Mach. Intell., vol. 35, no. 1, pp. 221-231, January 2013.

[28] Y. Fang, N. Yu, R. Wang, and D. Su, "An on-chip instrument for white blood cells classification based on a lens-less shadow imaging technique," PLoS One, vol. 12, no. 3, p. e0174580, March 2017.

[29] B. Storey et al., "Utilization of computer processed high definition video imaging for measuring motility of microscopic nematode stages on a quantitative scale: 'The Worminator,'" Int. J. Parasitol. Drugs Drug Resist., vol. 4, no. 3, pp. 233-243, December 2014.

[30] N. Mor, Ü. Y. Tekdoğan, and M. Bağcioğlu, "Parasitic Diseases of Urinary Tract," MIDDLE BLACK SEA J. Heal. Sci., vol. 2, no. 3, pp. 11-18, 2016.

What is claimed is:

1. An optofluidic device for detecting a presence of an analyte in a fluid sample, the optofluidic device comprising:
a microfluidic module having a microfluidic channel, the microfluidic channel having an upper surface, a lower surface and two opposed side surfaces each coupled to and extending between the upper surface and the lower surface, the microfluidic channel being configured to receive the fluid sample at an inlet thereof and direct the fluid sample towards an outlet thereof;
an image sensor removably abutting the microfluidic module, the image sensor being positioned laterally between the inlet and the outlet and below the lower surface of the microfluidic channel, the image sensor being communicatively coupled to a processor configured to receive signal data from the image sensor, the microfluidic module being positioned above the image sensor and a lower surface of the microfluidic module removably abutting a top surface of the image sensor; and
a light source configured to direct light through the fluid sample and towards the image sensor as the fluid sample passes through the microfluidic channel, the image sensor being configured to receive the light after it passes through the fluid sample and output the signal data to the processor to be used by the processor to detect the presence of the analyte in the fluid sample.

2. The optofluidic device of claim 1, wherein the lower surface of the microfluidic module is unadhered to the top surface of the image sensor providing for the microfluidic module to be replaceable.

3. The optofluidic device of claim 2, wherein the microfluidic module is positioned between the light source and the image sensor.

4. The optofluidic device of claim 1, wherein the light source is a non-coherent light source.

5. The optofluidic device of claim 1 further comprising a clamping system configured to maintain the microfluidic module and the image sensor in pressurized contact with each other.

6. The optofluidic device of claim 5, wherein the clamping system is configured to apply a downward force on the microfluidic module and an upward force on the image sensor to maintain the microfluidic module and the image sensor in the pressurized contact with each other.

7. The optofluidic device of claim 5, wherein the clamping system is configured to maintain the microfluidic module and the image sensor in the pressurized contact with each other and to release the microfluidic module and the image sensor from each other after the fluid sample flows through the microfluidic channel.

8. The optofluidic device of claim 1, wherein the microfluidic module includes a top layer and a bottom layer, the top layer being plasma bonded to the bottom layer and the bottom layer having a thickness that is less than or equal to 20 mm.

9. The optofluidic device of claim 1, wherein the processor is configured to:
   receive the signal data from the image sensor; and
   based on the signal data, detect the presence of the analyte in the fluid sample.

10. The optofluidic device of claim 9, wherein the processor is configured to detect the presence of the analyte in the fluid sample by:
    converting the signal data from the image sensor to image data;
    creating a video based on the image data; and
    analyzing features of the video to detect the presence of the analyte.

11. The optofluidic device of claim 10, wherein the processor is configured to analyze features of the video by operating a tracking algorithm.

12. The optofluidic device of claim 11, wherein the processor is further configured to analyze one or more frames of the video to detect moving objects in the video.

13. The optofluidic device of claim 12, wherein the processor is further configured to, based on summing multiple frames of the video, detect the presence of the analyte based on motion-based biomarkers of the analyte.

14. The optofluidic device of claim 13, wherein the analyte is *Trichomonas vaginalis* and the processor is configured to detect the presence of the *Trichomonas vaginalis* based on motion-based biomarkers specific to *Trichomonas vaginalis*.

15. The optofluidic device of claim 13, wherein the analyte has a non-spherical shape and the processor is configured to measure an elliptical ratio of shadow images of the analyte over multiple frames of the video to detect the presence of the analyte.

16. The optofluidic device of claim 15, wherein the analyte is red blood cells or white blood cells.

17. The optofluidic device of claim 13, wherein the analyte is a bacteria and the processor is configured to detect the presence of the bacteria based on motion-based biomarkers specific to the bacteria acquired over multiple frames of the video.

18. The optofluidic device of claim 13, wherein the analyte is smaller than a height of the microfluidic channel to provide for it to flow freely through the microfluidic channel.

19. A method of detecting a presence of an analyte in a fluid sample, the method comprising:
    forming a microfluidic module having a microfluidic channel, the microfluidic channel having an upper surface, a lower surface and two opposed side surfaces each coupled to and extending between the upper surface and the lower surface, the microfluidic channel being configured to receive the fluid sample at an inlet thereof and direct the fluid sample towards an outlet thereof;
    positioning an image sensor between the inlet and the outlet and below the lower surface of the microfluidic channel, the microfluidic module being positioned above the image sensor and a lower surface of the microfluidic module removably abutting a top surface of the image sensor, the image sensor being communicatively coupled to a processor configured to receive signal data from the image sensor;
    directing the fluid sample through the microfluidic channel; and
    directing light from a light source through the fluid sample and towards the image sensor as the fluid sample passes through the microfluidic channel, the image sensor being configured to receive the light after it passes through the fluid sample and output the signal data to the processor to be used by the processor to detect the presence of the analyte in the fluid sample.

20. An optofluidic device for detecting a presence of an analyte in a fluid sample, the optofluidic device comprising:
    a microfluidic module having a microfluidic channel, the microfluidic channel having an upper surface, a lower surface and two opposed side surfaces each coupled to and extending between the upper surface and the lower surface, the microfluidic channel being configured to receive the fluid sample at an inlet thereof and direct the fluid sample towards an outlet thereof;
    an image sensor removably abutting the microfluidic module, the image sensor being positioned laterally between the inlet and the outlet and below the lower surface of the microfluidic channel, the image sensor being communicatively coupled to a processor configured to receive signal data from the image sensor; and
    a light source configured to direct light through the fluid sample and towards the image sensor as the fluid sample passes through the microfluidic channel, the image sensor being configured to receive the light after it passes through the fluid sample and output the signal data to the processor to be used by the processor to detect the presence of the analyte in the fluid sample;
    wherein the processor is configured to:
      receive the signal data from the image sensor; and
      based on the signal data, detect the presence of the analyte in the fluid sample by:
        converting the signal data from the image sensor to image data
        creating a video based on the image data; and
        analyzing, by operating a tracking algorithm, features of the video to detect the presence of the analyte; and
    wherein the processor is further configured to:
      analyze one or more frames of the video to detect moving objects in the video; and
      based on summing multiple frames of the video, detect the presence of the analyte based on motion-based biomarkers of the analyte.

\* \* \* \* \*